US011015023B2

(12) United States Patent
Pyun

(10) Patent No.: US 11,015,023 B2
(45) Date of Patent: May 25, 2021

(54) FIRE RETARDANT COMPOSITIONS UTILIZING ELEMENTAL SULFUR

(71) Applicant: ARIZONA BOARD OF REGENTS ON BEHALF OF THE UNIVERSITY OF ARIZONA, Tucson, AZ (US)

(72) Inventor: Dong-Chul Pyun, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 16/512,809

(22) Filed: Jul. 16, 2019

(65) Prior Publication Data

US 2019/0338076 A1 Nov. 7, 2019

Related U.S. Application Data

(63) Continuation-in-part of application No. 15/739,525, filed on Dec. 22, 2017, now abandoned, and a (Continued)

(51) Int. Cl.

*C08G 75/16* (2006.01)
*C01B 17/96* (2006.01)

(Continued)

(52) U.S. Cl.

CPC ............ *C08G 75/16* (2013.01); *A01N 41/12* (2013.01); *A01N 59/02* (2013.01); *A61K 31/795* (2013.01);

(Continued)

(58) Field of Classification Search

CPC ........ C08G 75/16; C08G 75/14; C01B 17/96; C01B 3/042; A61K 31/795; A01N 41/12;

(Continued)

(56) References Cited

U.S. PATENT DOCUMENTS 2,779,761 A 1/1957 Kibler
2,989,513 A * 6/1961 Hendry .................... C08L 7/00 525/332.6

(Continued)

FOREIGN PATENT DOCUMENTS

CN 104713968 A1 6/2015
EP 0806451 A1 11/1997

(Continued)

OTHER PUBLICATIONS

Chung, W.J. et al., "Elemental Sulfur as a Reactive Medium for Gold Nanoparticles and Nanocomposite Materials", Angewandte Chemie International Edition, 2011, 50, 11409-11412.

(Continued)

*Primary Examiner* — Andrew J. Oyer
(74) *Attorney, Agent, or Firm* — Nguyen Tarbet LLC

(57) ABSTRACT

Compositions of flame retardants and methods of enhancing char formation in a flame retardant-treated substrate. A base material is combined with a flame retardant to form the flame retardant-treated substrate. The flame retardant contains a sulfur copolymer prepared by the polymerization of sulfur monomers with organic monomers. The flame retardant can be deposited on a surface of the base material, coated on the base material, or mixed into the base material. When the flame resistant substrate is on fire, the flame retardant forms a charring layer on the flame retardant-treated substrate. The charring layer can extinguish and prevent the fire from spreading.

12 Claims, 3 Drawing Sheets

DIB20 Tc=800°C DIB30 Tc=800°C DIB50 Tc=800°C

Related U.S. Application Data continuation-in-part of application No. 15/287,118, filed as application No. PCT/US2016/040067 on Jun. 29, 2016, now Pat. No. 10,833,330, and a continuation of application No. 14/622,429, filed on Feb. 13, 2015, now Pat. No. 9,567,439, which is a continuation-in-part of application No. 14/237,659, filed as application No. PCT/US2012/050602 on Aug. 13, 2012, now Pat. No. 9,306,218.

(60) Provisional application No. 62/186,618, filed on Jun. 30, 2015, provisional application No. 62/039,588, filed on Aug. 20, 2014, provisional application No. 62/039,561, filed on Aug. 20, 2014, provisional application No. 62/017,750, filed on Jun. 26, 2014, provisional application No. 61/940,102, filed on Feb. 14, 2014, provisional application No. 61/685,847, filed on Mar. 26, 2012, provisional application No. 61/574,957, filed on Aug. 12, 2011, provisional application No. 61/574,903, filed on Aug. 11, 2011.

(51) Int. Cl.

| | |
|---|---|
| ***A61K 31/795*** | (2006.01) |
| ***A01N 41/12*** | (2006.01) |
| ***H01M 4/60*** | (2006.01) |
| ***C08L 81/04*** | (2006.01) |
| ***A01N 59/02*** | (2006.01) |
| ***C01B 3/04*** | (2006.01) |
| ***H01M 10/052*** | (2010.01) |
| ***H01M 4/38*** | (2006.01) |
| ***C08G 75/14*** | (2006.01) |

(52) U.S. Cl.
CPC .............. *C01B 3/042* (2013.01); *C01B 17/96* (2013.01); *C08L 81/04* (2013.01); *H01M 4/606* (2013.01); *C08G 75/14* (2013.01); *C08L 2201/52* (2013.01); *H01M 4/382* (2013.01); *H01M 10/052* (2013.01); *Y02E 60/36* (2013.01)

(58) Field of Classification Search
CPC ..... A01N 59/02; C08L 81/04; C08L 2201/52; Y02E 60/36; H01M 10/052; H01M 4/382; H01M 4/628; H01M 10/4235; H01M 4/606
See application file for complete search history.

(56) References Cited

U.S. PATENT DOCUMENTS

| | | | | |
|---|---|---|---|---|
| 3,251,797 | A | 5/1966 | De Pugh et al. | |
| 3,290,266 | A | 12/1966 | Barnes et al. | |
| 3,542,701 | A | 11/1970 | van Raamsdonk | |
| 3,563,962 | A | 2/1971 | Mirviss | |
| 3,767,613 | A | 10/1973 | Dix et al. | |
| 3,892,686 | A | 7/1975 | Woo | |
| 4,000,347 | A | 12/1976 | Ranney et al. | |
| 4,094,751 | A | 6/1978 | Nozik | |
| 4,238,585 | A | 12/1980 | Bertozzi | |
| 4,346,191 | A | 8/1982 | Blount | |
| 4,382,846 | A | 5/1983 | Gratzel et al. | |
| 4,568,435 | A | 2/1986 | Shelnutt | |
| 4,606,798 | A | 8/1986 | Sasse et al. | |
| 4,671,896 | A | 6/1987 | Hasegawa et al. | |
| 4,739,036 | A * | 4/1988 | Colvin ................ | C07G 17/004 528/389 |
| 4,740,559 | A * | 4/1988 | Johansson ............. | C08G 75/00 525/185 |
| 4,749,347 | A | 6/1988 | Valavaara | |
| 4,752,507 | A | 6/1988 | Johansson et al. | |
| 4,833,048 | A | 5/1989 | DeJonghe et al. | |
| 5,115,060 | A | 5/1992 | Grey | |
| 5,121,329 | A | 6/1992 | Crump | |
| 5,279,910 | A | 1/1994 | Sasaki et al. | |
| 5,371,176 | A | 6/1994 | Bezwada et al. | |
| 5,362,493 | A | 11/1994 | Skotheim et al. | |
| 5,811,470 | A | 9/1998 | Prindle et al. | |
| 5,929,202 | A | 7/1999 | Arita et al. | |
| 6,011,094 | A | 1/2000 | Planche et al. | |
| 6,072,026 | A | 6/2000 | Kawase et al. | |
| 6,111,030 | A | 8/2000 | Hartman et al. | |
| 9,306,218 | B2 | 4/2016 | Pyun et al. | |
| 9,463,597 | B2 | 10/2016 | Van De Vrie et al. | |
| 9,567,439 | B1 | 2/2017 | Pyun et al. | |
| 2001/0047043 | A1 | 11/2001 | Okoroafor et al. | |
| 2001/0047403 | A1 | 11/2001 | Okoroafor et al. | |
| 2002/0039680 | A1 | 4/2002 | Hwang et al. | |
| 2003/0060567 | A1 * | 3/2003 | Faderl ................ | C08L 2666/04 525/154 |
| 2007/0010600 | A1 | 1/2007 | Goodman et al. | |
| 2007/0253772 | A1 | 11/2007 | Kubo et al. | |
| 2008/0038645 | A1 | 2/2008 | Kolosnitsyn et al. | |
| 2010/0029163 | A1 | 2/2010 | Ogle et al. | |
| 2011/0245360 | A1 | 10/2011 | Hahn et al. | |
| 2011/0263755 | A1 | 10/2011 | Mohamed et al. | |
| 2012/0264837 | A1 | 10/2012 | Eberstaller et al. | |
| 2013/0040197 | A1 | 2/2013 | Liu et al. | |
| 2013/0064904 | A1 | 3/2013 | Gojon-Romanillos et al. | |
| 2014/0110881 | A1 | 4/2014 | Keledjian et al. | |
| 2014/0199592 | A1 | 7/2014 | Pyun et al. | |
| 2015/0203638 | A1 | 7/2015 | Sivanandan et al. | |
| 2018/0079865 | A1 | 3/2018 | Pyun | |
| 2018/0105649 | A1 | 4/2018 | Pyun et al. | |

FOREIGN PATENT DOCUMENTS

| | | | |
|---|---|---|---|
| EP | 1882713 | A1 | 1/2008 |
| EP | 2093605 | A1 | 8/2009 |
| EP | 2896644 | A1 | 7/2015 |
| GB | 1203577 | A | 8/1970 |
| GB | 1516554 | A | 7/1978 |
| WO | WO1995018652 | A1 | 7/1995 |
| WO | WO2007076067 | A3 | 7/2007 |
| WO | WO2009158385 | A | 12/2009 |
| WO | WO2013023216 | A1 | 2/2013 |
| WO | WO2013155038 | A1 | 10/2013 |
| WO | WO2014052255 | A1 | 4/2014 |
| WO | WO2014179100 | A1 | 11/2014 |
| WO | WO2015123552 | A1 | 8/2015 |

OTHER PUBLICATIONS

Colquhoun, Howard M., “Materials that heal themselves”, Nature Chemistry, Jun. 2012, vol. 4, 435-436.

Yang, Ying and Urban Marek W., “Self-healing polymeric materials”, Chem. Soc. Rev., 2013, 42, 7446-7467.

Hasegawa, Urara and Van Der Vlies, AndréJ., “Design and Synthesis of Polymeric Hydrogen Sulfide Donors”, Bioconjugate Chemistry, 2014, 25 (7), 1290-1300.

Foster, Jeffrey C., et al., “S-Aroylthiooximes: A Facile Route to Hydrogen Sulfide Releasing Compounds with Structure-Dependent Release Kinetics”, Organic Letters. 2014, 16, 1558-1561.

Wurthner, F., “Perylene bisimide dyes as versatile building blocks for functional supramolecular architectures”, Chem. Commun. 2004, 1564-1579.

Chung, W.-. et al., “The use of elemental sulfur as an alternative feedstock for polymeric materials”, Nature Chemistry 2013, vol. 5, 518-524.

Simmonds, A.G. et al., “Inverse Vulcanization of Elemental Sulfur to Prepare Polymeric Electrode Materials for Li—S Batteries”, ACS Macro Lett. 2014, 3, 229-232.

Liu, G. et al., “α-Sulfur Crystals as a Visible-Light-Active Photocatalyst”, J. Am. Chem. Soc. 2012, 134, 9070-9073.

Asmus, K.-D., “Pulse Radiolysis Methodology”, Methods in Enzymology 1984, 105, 167-178.

(56) References Cited

OTHER PUBLICATIONS

Nishide, et al., "Toward Flexible Batteries", (2008) Science, vol. 319, 737-738.
Nishide, et al., "Emerging N-Type Redox-Active Radical Polymer for a Totally Organic Polymer-Based Rechargeable Battery", (2009), Adv Mater, 21, 1627-1630.
Tarascon, et al., "Key challenges in future Li-battery research", (2010) Phil Trans R Soc A, 368, 3227.
Rotinjanz, et al. (1908) Z. Physik Chem, 62, 609.
Bacon, et al., "The Viscosity of Sulfur", (1943) J Am Chem Soc, 65, 639.
Eyring, et al., "The Properties of Liquid Sulfur", (1943) J Am Chem 65, 648.
Tobolsky, A. V. et al., "Equilibrium Polymerization of Sulfur", Am. Chem. Soc.1959, 81, 780.
Penczek, et al. (1974) Nature, 273, 738.
Nazar et al., "A highly ordered nanostructured carbon-sulphur cathode for lithium-sulphur batteries", Nature Mater. 2009, 8, 500-506.
Scrosati, et al., "A High-Performance Polymer Tin Sulfur Lithium Ion Battery", Angew. Chem. Int. Ed. 2010, 49, 2371-2374.
Chen, et al., J. Phys. Chem. C 2011, 115, 6057-6063.
Yang, et al., ACS Nano 2011, 5, 9187-9193.
Bartlett, et al., (1956) J Am Chem Soc, 78, 3710.
Mcgrath, et al. (2006) Polymer, 47, 4042.
Ueda et al., (2009) J Mater Chem, 19, 8907.
Trofimov, et al. (2002) "Sulfur-rich copolymers of sulfur with 5-vinylbicyclo hept-2-ene and tricyclo deca-3,8-diene as prospective cathode materials for lithium cells," Sufur Letters, 25: 219-227.
Ning, et al., (2004) "Novel cathode material based on chloropolystyrene," PMSE Preprints, American Chemical Society 90: 396-397.
Wang, et al., Nano Lett. 2011, 11, 2644-2647.
Zheng, et al., Nano Lett. 2011, 11, 4462-4467.
Li, et al, Proc. Nail. Acad. Sci. U.S.A. 2013, 110, 7148-7153.
Zheng, et al., Nano Lett. 2013, 13, 1265-1270.
Zhou, et al., ACS Nano 2013, 7, 8801-8808.
Seh, et al., Nat. Commun. 2013, 4.
Li, et al., Nano Lett. 2013, 13, 5534.
Liu, et al., Nat. Nanolech. 2014, 9, 187.
Pyun, J. Angew. Chem Int. Ed., 2011, 50, 11409-11412.
Woo et al. Nature Chemistry. Jun. 2013. vol. 5, pp. 518-524. Published online Apr. 14, 2013.
Suzuki et al. Hydrogen generation using water-insoluble polymer-bound ruthenium(ii) Complexes. Chemical Communications, 1997, Issue 2, p. 227.
Suzuki et al. Photoinduced hydrogen generation from water-insoluble polymer photosensitizer films. Polymer, 1998, vol. 39, Issue 8, p. 1539-1543.
Suzuki et al. Photoinduced hydrogen generation using polymer photosensitizers. Macromolecular Chemistry and Physics, Jun. 1998, vol. 199, Issue 6.
Wang et al. A metal-free polymeric photocatalyst for hydrogen production from water under visible light. Nature Materials 8, 76-80 (2009).
Goldsmith et al. Discovery and High-Throughput Screening of Heteroleptic Iridium Complexes for Photoinduced Hydrogen Production. J. Am. Chem. Soc., 2005, 127 (20), pp. 7502-7510.
Tinker et al. Visible Light Induced Catalytic Water Reduction without an Electron Relay. Chemistry—A European Journal, 2007, vol. 13, Issue 31, pp. 8726-8732.
Happ et al. Towards Hydrogen Evolution Initiated by LED Light: 2-(1 H-1,2,3-Triazol-4-yl)pyridine containing Polymers as Photocatalyst. Macromolecular Rapid Communications, Apr. 2015, vol. 36, Issue 7, 671-677.
Aguirre De Carcer et al. Active-Site Models for Iron Hydrogenases: Reduction Chemistry of Dinuclear Iron Complexes. Inorg. Chem., 2006, 45 (20), pp. 8000-8002.
Alongia et al. Caseins and hydrophobins as novel green flame retardants for cotton fabrics. Polymer Degradation and Stability vol. 99, Jan. 2014, pp. 111-117.
Beom-Young Ryu and Todd Emrick. Thermally Induced Structural Transformation of Bisphenol-1,2,3-triazole Polymers: Smart, Self-Extinguishing Materials. Angew. Chem. Int. Ed. 2010, 49, 9644-9647.
Laufer et al. Clay-Chitosan Nanobrick Walls: Completely Renewable Gas Barrier and Flame-Retardant Nanocoatings. ACS Appl. Mater Interfaces 2012, 4, 1643-1649.
Laufer et al. Exceptionally Flame Retardant Sulfur-Based Multilayer Nanocoating for Polyurethane Prepared from Aqueous Polyelectrolyte Solutions. ACS Macro Lett., 2013, 2 (5), pp. 361-365.
Li et al. Intumescent All-Polymer Multilayer Nanocoating Capable of Extinguishing Flame on Fabric. Adv. Mater. 2011, 23, 3926-3931.
Ding et al. Photoelectrocatalytic Water Splitting: Significance of Cocatalysts, Electrolyte, and Interfaces. ACS Catal. 2017, 7, 675-688.
Swenson, M. Synthesis and Characterization of [Fe Fe) Hydrogenase Mimics. The University of Arizona, 2013, pp. 1-157 online), [retrieved on Jan. 19, 2018). Retrieved from the Internet <http://arizona.openrepository.com/arizona/handle/1 0150/294029>.

* cited by examiner

DIB20 Tc=800°C

DIB30 Tc=800°C

DIB50 Tc=800°C

FIRE RETARDANT COMPOSITIONS UTILIZING ELEMENTAL SULFUR

CROSS REFERENCE

This application is a continuation-in-part and claims benefit of U.S. patent application Ser. No. 15/739,525 filed Dec. 22, 2017, which is a 371 of International Application No. PCT/US16/40067 filed Jun. 29, 2016, which claims benefit of U.S. Provisional Application No. 62/186,618 filed Jun. 30, 2015, the specification(s) of which is/are incorporated herein in their entirety by reference.

This application is a continuation-in-part and claims benefit of U.S. patent application Ser. No. 15/287,118 filed Oct. 6, 2016, which is a continuation and claims benefit of U.S. patent application Ser. No. 14/622,429 filed Feb. 13, 2015, now U.S. Pat. No. 9,567,439, which claims benefit of U.S. Provisional Application No. 62/039,588 filed Aug. 20, 2014, U.S. Provisional Application No. 62/039,561 filed Aug. 20, 2014, U.S. Provisional Application No. 62/017,750 filed Jun. 26, 2014, and U.S. Provisional Application No. 61/940,102 filed Feb. 14, 2014, the specification(s) of which is/are incorporated herein in their entirety by reference.

Furthermore, U.S. patent application Ser. No. 14/622,429 is a continuation-in-part and claims benefit of U.S. patent application Ser. No. 14/237,659 filed Mar. 11, 2014, now U.S. Pat. No. 9,306,218, which is a 371 of International Application No. PCT/US12/50602 filed on Aug. 13, 2012, which claims benefit of U.S. Provisional Application No. 61/685,847 filed Mar. 26, 2012, U.S. Provisional Application No. 61/574,957 filed Aug. 12, 2011, and U.S. Provisional Application No. 61/574,903 filed Aug. 11, 2011, the specification(s) of which is/are incorporated herein in their entirety by reference.

FIELD OF THE INVENTION

The present invention relates to flame retardants, in particular, to a high sulfur content polymer having flame retardant properties.

BACKGROUND OF THE INVENTION

Elemental sulfur ($S_8$) is generated as a waste byproduct from hydrodesulfurization of crude petroleum feedstocks. Current industrial utilization of elemental sulfur is centered around sulfuric acid, agrochemicals, and vulcanization of rubber. For example, elemental sulfur is used primarily for sulfuric acid and ammonium phosphate fertilizers, whereas the rest of the excess sulfur is stored as megaton-sized, above ground sulfur towers. In its original state, elemental sulfur is a cyclic molecule forming a brittle, intractable, crystalline solid having poor solid state mechanical properties, poor solution processing characteristics. While sulfur feedstocks are plentiful, sulfur is difficult to process. Before the invention of the inverse vulcanization process, which is described in U.S. Pat. Nos. 9,567,439 and 9,306,218, the specifications of which are incorporated herein in their entirety by reference, there was only a limited number of synthetic methods available to utilize and modify elemental sulfur. Hence, there is a need for the production of new materials and use thereof to mitigate the storage of excess sulfur.

Synthetic polymers are often highly flammable and often do not meet fire safety standards on their own. Polymers, such as polyurethane foams used in furniture cushions and polymers used in electrical applications or for personal protective equipment (PPE), such as those used by firefighters, must be treated to be flame retardant. For example, the Occupational Safety and Health Administration (OSHA) can cite employers for code violations if employees who are exposed to electric arcs or flame are found to wear any clothing that is not flame resistant or flame-retardant-treated, if said clothing can ignite under the electric arc and flame exposure conditions found at the workplace. Moreover, OSHA prohibits the use of clothing constructed from acetate, nylon, polyester, rayon, or blends thereof unless the fabric is demonstrated to have been treated to withstand the conditions that may be encountered, that is, made flame resistant or flame-retardant-treated. Flame resistant protective garments are designed to be used in a variety of industrial applications in order to reduce or prevent the severity or fatality of burns caused by fire hazards.

In order to meet fire safety standards, synthetic polymers that are often highly flammable must be treated with toxic compounds to be flame retardant. For instance, fire safety guidelines require the use of flame retardant chemicals for treating polyurethane foams, which is highly flammable, and when burned, melts at higher temperatures and further spreads the fire. According to the US National Fire Protection Association, furniture and bedding were the first objects to catch fire in an average of 17,300 fires annually, which have resulted in 871 civilian deaths and damage to property worth millions of dollars. According to a report published by the US National Fire Protection Association, soft foam-based home furniture and upholstered furniture were the items that initiated the ignition in about 20% of home fire-related deaths that occurred from 2006 to 2010.

These flame retardant chemicals are toxic and harmful to human health and the environment. Most of the current flame-retardant materials are based on halogenated compounds and many of them have been already banned due to concerns over their potential toxicity. Toxic chemicals, such as polyurethane foam and some brominated compounds have been shown to act as endocrine disrupters or lead to neurological problems. Hence, regulatory agencies, such as those in the European Union, Canada, and the United States, have begun to scrutinize the use of these chemicals.

For these reasons, there is a strong need for flame retardant material to protect foam-based furniture, as well as other highly flammable polymers, from catching fire. Recent advancements have occurred in the past few years in the flame retardant polymers industry and as safety standards become more stringent, the importance of finding non-toxic flame retardant polymers continues to grow.

Standards for testing flammability can determine the effectiveness of a flame retardant. As with any testing, the tests for flammability of a specimen are designed for the laboratory and quality control. Examples of such testing include Limiting Oxygen Index (LOI) and Underwriters Laboratory (UL94). The LOI test is a measure of the percentage of oxygen that has to be present to support combustion of the plastic. Since air contains approximately 21% oxygen, higher LOI values greater than 21 are desirable for indicating lower flammability.

The UL testing is a method of classifying a material's tendency to either extinguish or spread a flame once it has been ignited. This has been incorporated into many National and International Standards (ISO 9772 and 9773). For example, the UL vertical burning test (UL94-V) requires a specimen to be tested in a vertical orientation with the ignition placed at the lower end of the specimen. A UL94-V rating of V-1 is acceptable if the tests results in the following: duration of flaming for each flaming application is less than 30 seconds, the total duration of flaming for 5 samples (10 flame applications) is less than 250 seconds, and there is no dripping of flaming material. A UL94-V rating of V-0 is superior if the tests results in the following: duration of flaming for each flaming application is less than 10 seconds, the total duration of flaming for 5 samples (10 flame applications) is less than 50 seconds, and there is no dripping of flaming material.

U.S. Pat. No. 5,811,470 teaches a composition which comprises a styrenic polymer and as a flame retardant therefor, a combination of the following ingredients: at least one organic phosphorus additive that (i) is halogen-free, and (ii) is composed solely of carbon, hydrogen, and phosphorus, and optionally one or more of the elements nitrogen, oxygen, and sulfur; and elemental sulfur.

U.S. Pat. No. 3,542,701 discloses the manufacture of polystyrene foams of decreased inflammability which comprises incorporating from 5 to 35% by weight of elemental sulfur in a polystyrene bead precursor mix and expanding the mix to form a foam.

US20120264837 reports a halogen-free, flameproof expandable styrene polymers (EPS) and styrene polymer extruded foams (XPS) may be produced by admixing a blowing agent, one or more phosphorus compound(s) and elemental sulfur and/or a sulfur-containing compound or sulfur compound into the polymer melt and subsequent extrusion to give foam sheets, foam strands, or expandable granules.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The subject disclosure features a flame retardant composition comprising a sulfur copolymer. The sulfur copolymer is prepared using inverse vulcanization, thereby resulting in a sulfur copolymer having a high sulfur content. These sulfur-based polymers, also referred to as Chalcogenide Hybrid Inorganic/Organic Polymers (CHIPs), can form high char content, self-extinguishing materials upon pyrolysis. The present invention may be used to treat polymers, such as polyurethane, commonly used in applications that require fire retardant properties or in personal protective equipment.

For example, in some embodiments, CHIPs based on vinylic comonomers, such as styrene and 1,3-diisopropenylbenzene (DIB), can be co-formulated with other known structural polymers to form outer coatings that can serve as flame retardant barriers. In other embodiments, polymer blending approaches may be used to prepare flame retardant polymeric materials. Methods for polymer blending CHIPs with other materials include solution blending, melt processing and co-extrusion. These fabrication methods include use of these polymer-CHIPs blends as filaments for 3-D printing and other additive manufacturing processes. In some embodiments, any thermoplastic, melt-processable, solution-processable polymer may be used for co-formulation with CHIPs materials to produce flame retardant polymeric materials.

One of the unique and inventive technical features of the present invention is that the flame retardant composition comprising a sulfur copolymer having a high sulfur content was surprisingly found to have higher char yields than other synthetic polymers. Without wishing to limit the invention to any theory or mechanism, it is believed that the technical feature of the present invention advantageously provides for a more effective flame retardant that is non-halogenated. Further still, the present invention allows for the direct use of low cost elemental sulfur to form inexpensive high sulfur content copolymers that can promote a higher carbon char content than other prior arts. The sulfur copolymers described herein are readily solution, or melt processed into thin films, coatings, or blends for use as a flame retardant.

According to one embodiment, the present invention features a fire retardant composition comprising a sulfur copolymer. The sulfur copolymer may comprise at least about 40 wt % sulfur monomers, and about 10 wt % to 50 wt % of organic comonomers, wherein the organic comonomers are polymerized with the sulfur monomers.

According to another embodiment, the present invention features a fire retardant composition comprising a polymeric blend of at least about 50 wt % of a thermoplastic polymer, and about 10-50 wt % of a sulfur copolymer. The sulfur copolymer may comprise at least about 40 wt % of sulfur monomers, and about 10-50 wt % of organic comonomers that are polymerized with the sulfur monomers.

In some embodiments, the sulfur monomers are prepared from elemental sulfur. In other embodiments, the organic comonomers used in herein may be selected from a group consisting of amine monomers, thiol monomers, sulfide monomers, alkynylly unsaturated monomers, epoxide monomers, nitrone monomers, aldehyde monomers, ketone monomers, thiirane monomers, and ethylenically unsaturated monomers.

In some embodiments, the fire retardant composition may be used as a fire retardant intumescent coating. Without wishing to be bound by theory or mechanism, when a substrate combined with the fire retardant composition is on fire, the fire retardant composition can form a charring layer on a surface of the substrate that is effective for extinguishing the fire. The charring layer comprises at least about 10 wt % char or at least about 20 wt % char. In some preferred embodiments, the fire retardant composition may provide for test specimens that are combined with the fire retardant composition to exhibit a limiting oxygen index (LOI) of at least 25 and a UL94-V rating of V-1 or V-0.

Another embodiment featuring a method of enhancing char formation in a substrate is described herein. The method may comprise combining a base material with a fire retardant composition to form the substrate. The fire retardant composition may be deposited on a surface of the base material, coated on the base material, or mixed into the base material. Preferably, when the substrate is on fire, the fire retardant composition forms a charring layer on the substrate, thereby extinguishing and preventing the fire from spreading.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

Figure 1:
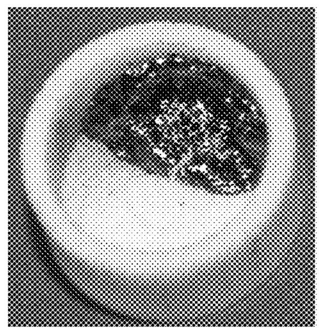
FIG. 1 shows examples of charred samples of the present invention for a combustor temperature of 800° C.
Figure 1:
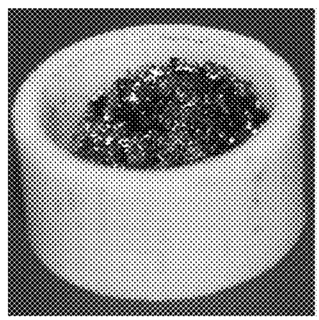
Figure 1:
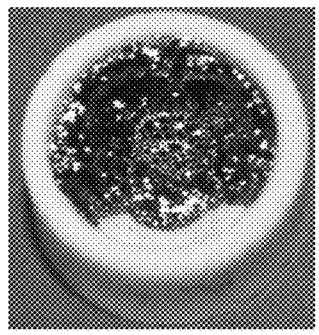
Figure 1:
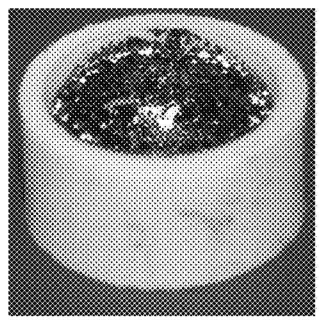
Figure 1:
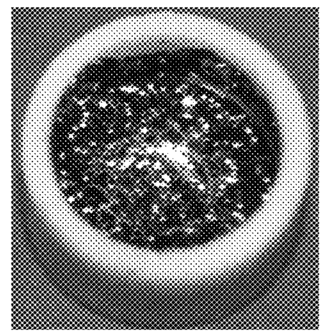
Figure 1:
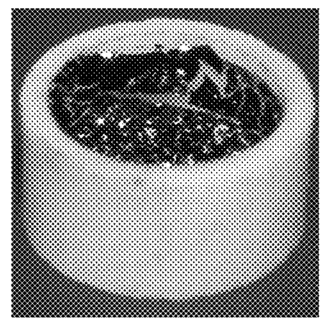

As used herein, the term "char" is defined as a carbonaceous residue resulting from the conversion of an organic matter, usually through pyrolysis. Char formation results from the action of substances which are able to reticulate a burning substrate and to create a charring insulating layer.

As used herein, the term "intumescence" is defined as a mechanism that creates a foamed charring structure which forms a barrier to prevent flame and oxygen from reaching a substrate. Typically, an intumescent substance will swell as a result of heat exposure, thus increasing in volume and decreasing in density. When heated, an intumescent can produce charring.

As used herein, the term "amine monomer" is a monomer having at least one amine functional group. The amine monomer may be polymerizable through its amine functional group. In one embodiment, aromatic amines and multi-functional amines may be used. Amine monomers include, but are not limited to, m-phenylenediamine, and p-phenylenediamine. The various types of phenylenediamines are inexpensive reagents due to their wide-spread use in the preparation of many conventional polymers, e.g., polyurethanes, polyamides. In the reaction of 1,3-phenylenediamine with $S_8$ a surprising substitution of the aromatic ring with sulfur groups in the copolymerization. Furthermore, the resulting sulfur copolymer carried reactive amine moieties that were further reacted with comonomers, such as, isocyanates, acid chlorides, epoxides, carboxylic acids, esters, amides, alkyl halides, or acrylates to either modify the sulfur copolymer, or make new copolymeric materials, such as, polyamides, polyurethanes, polyamides, and polyethers.

As used herein, the term "thiol monomer" is a monomer having at least one thiol functional group. The thiol monomer may be polymerizable through its thiol functional group. Thiol monomers include, but are not limited to, 4,4'-thiobisbenzenethiol and the like. The term "sulfide monomers" are those that have at least one sulfide functional group. The sulfide monomers may be polymerizable through its sulfide functional group.

As used herein, an alkynylly unsaturated monomer is a monomer having at least alkynylly unsaturated functional group. The alkynylly unsaturated monomer may be polymerizable through its alkynyl unsaturation (i.e., its triple bond). The term "alkynylly unsaturated monomer" does not include compounds in which the alkynyl unsaturation is part of a long chain alkyl moiety (e.g., unsaturated fatty acids, or carboxylic salts, or esters such as oleates, and unsaturated plant oils). In one embodiment, aromatic alkynes, both internal and terminal alkynes, multi-functional alkynes may be used. Examples of alkynylly unsaturated monomers include, but are not limited to, ethynylbenzene, 1-phenylpropyne, 1,2-diphenylethyne, 1,4-diethynylbenzene, 1,4-bis (phenylethynyl)benzene, and 1,4-diphenylbuta-1,3-diyne.

As used herein, the term "nitrone monomer" is a monomer having at least one nitrone functional group. The nitrone monomer may be polymerizable through its nitrone functional group. In one embodiment, nitrones, dinitrones, and multi-nitrones may be used. Examples include, but are not limited to, N-benzylidene-2-methylpropan-2-amine oxide.

As used herein, the term "aldehyde monomer" is a monomer having at least one aldehyde functional group. The aldehyde monomer may be polymerizable through its aldehyde functional group. In one embodiment, aldehydes, dialdehydes, and multi-aldehydes may be used.

As used herein, a "ketone monomer" is a monomer with at least one ketone functional group. The ketone monomer may be polymerizable through its ketone functional group. In one embodiment, ketones, dikitones, or multi-ketones may be used.

As used herein, the term "epoxide monomer" is a monomer having at least one epoxide functional group. The epoxide monomer may be polymerizable through its epoxide functional group. Non-limiting examples of such monomers include, generally, mono- or polyoxiranylbenzenes, mono- or polyglycidylbenzenes, mono- or polyglycidyloxybenzenes, mono- or polyoxiranyl(hetero)aromatic compounds, mono- or polyglycidyl(hetero)aromatic compounds, mono- or polyglycidyloxy(hetero)aromatic compounds, diglycidyl bisphenol A ethers, mono- or polyglycidyl(cyclo)alkyl ethers, mono- or polyepoxy(cyclo)alkane compounds and oxirane-terminated oligomers. In one preferred embodiment, the epoxide monomers may be benzyl glycidyl ether and tris(4-hydroxyphenyl)methane triglycidyl ether. In certain embodiments, the epoxide monomers may include a (hetero)aromatic moiety such as, for example, a phenyl, a pyridine, a triazine, a pyrene, a naphthalene, or a polycyclic (hetero)aromatic ring system, bearing one or more epoxide groups. For example, in certain embodiments, the one or more epoxide monomers are selected from epoxy(hetero) aromatic compounds, such as styrene oxide and stilbene oxide and (hetero)aromatic glycidyl compounds, such as glycidyl phenyl ethers (e.g., resorcinol diglycidyl ether, glycidyl 2-methylphenyl ether), glycidylbenzenes (e.g., (2,3-epoxypropyl)benzene) and glycidyl heteroaromatic compounds (e.g., N-(2,3-epoxypropyl)phthalimide). In certain desirable embodiments, an epoxide monomer will have a boiling point greater than 180° C., greater than 200° C., or even greater than 230° C. at the pressure at which polymerization is performed (e.g., at standard pressure, or at other pressures).

As used herein, the term "thiirane monomer" is a monomer having at least one thiirane functional group. The thiirane monomer may be polymerizable through its thiirane functional group. Non-limiting examples of thiirane monomers include, generally, mono- or polythiiranylbenzenes, mono- or polythiiranylmethylbenzenes, mono- or polythiiranyl(hetero)aromatic compounds, mono- or polythiiranylmethyl(hetero)aromatic compounds, dithiiranylmethyl bisphenol A ethers, mono- or polydithiiranyl (cyclo)alkyl ethers, mono- or polyepisulfide(cyclo)alkane compounds, and thiirane-terminated oligomers. In some embodiments, thiirane monomers may include a (hetero)aromatic moiety such as, for example, a phenyl, a pyridine, a triazine, a pyrene, a naphthalene, or a poly cyclic (hetero)aromatic ring system, bearing one or more thiirane groups. In certain desirable embodiments, a thiirane monomer will have a boiling point greater than 180° C., greater than 200° C., or even greater than 230° C. at the pressure at which polymerization is performed (e.g., at standard pressure).

As used herein, an ethylenically unsaturated monomer is a monomer having at least one ethylenically unsaturated functional group. The ethylenically unsaturated monomer may be polymerizable through its ethylenic unsaturation (i.e., its double bond). The term "ethylenically unsaturated monomer" does not include cyclopentadienyl species such as cyclopentadiene and dicyclopentadiene. The term "ethylenically unsaturated monomer" does not include compounds in which the ethylenic unsaturation is part of a long chain alkyl moiety (e.g. unsaturated fatty acids such as oleates, and unsaturated plant oils).

In certain embodiments, the one or more ethylenically unsaturated monomers are selected from the group consisting of vinyl monomers, (meth)acryl monomers, unsaturated hydrocarbon monomers, and ethylenically-terminated oligomers. Examples of such monomers include, generally, mono- or polyvinylbenzenes, mono- or polyisopropenylbenzenes, mono- or polyvinyl(hetero)aromatic compounds, mono- or polyisopropenyl(hetero)aromatic compounds, alkylene di(meth)acrylates, bisphenol A di(meth)acrylates, benzyl (meth)acrylates, phenyl(meth)acrylates, heteroaryl (meth)acrylates, terpenes (e.g., squalene) and carotene. As molten sulfur is non-polar in character, in certain desirable embodiments the one or more ethylenically unsaturated monomers are non-polar. For example, in certain embodiments, the one or more ethylenically unsaturated monomers include a (hetero)aromatic moiety such as, for example, phenyl, pyridine, triazine, pyrene, naphthalene, or a polycyclic (hetero)aromatic ring system, bearing one or more vinylic, acrylic or methacrylic substituents. Examples of such monomers include benzyl (meth)acrylates, phenyl (meth)acrylates, divinylbenzenes (e.g., 1,3-divinylbenzene, 1,4-divinylbenzene), isopropenylbenzene, styrenics (e.g., styrene, 4-methylstyrene, 4-chlorostyrene, 2,6-dichlorostyrene, 4-vinylbenzyl chloride), diisopropenylbenzenes (e.g., 1,3-diisopropenylbenzene), vinylpyridines (e.g., 2-vinylpyridine, 4-vinylpyridine), 2,4,6-tris((4-vinylbenzyl)thio)-1,3,5-triazine and divinylpyridines (e.g., 2,5-divinylpyridine). In certain embodiments, the one or more ethylenically unsaturated monomers (e.g., including an aromatic moiety) bears an amino (i.e., primary or secondary) group, a phosphine group or a thiol group. One example of such a monomer is vinyldiphenylphosphine. While not intending to be bound by theory, the inventors surmise that the amino or thiol group will undergo a ring-opening nucleophilic attack on an $S_8$ ring, thus incorporating a short sulfide chain that promotes solubility in molten sulfur. Of course, a person of skill in the art will identify other ethylenically unsaturated monomers that can be used in forming the copolymers described herein. In certain desirable embodiments, an ethylenically unsaturated monomer will have a boiling point greater than 180° C., greater than 200° C., or even greater than 230° C. at the pressure at which polymerization is performed (e.g., at standard pressure).

As used herein, an "elemental carbon material" is a material that is primarily formed as an allotrope of carbon, with a minor amount of chemical modification. For example, graphene, graphene oxide, graphite, carbon nanotubes, fullerenes, carbon black, carbon flakes and carbon fibers are examples of elemental carbon materials. Such materials can be made, for example, by first dispersing the elemental carbon material in molten sulfur, then copolymerizing the molten sulfur with one or more monomers (e.g., one or more polyfunctional monomers). As a general guideline for the person of skill in the art to use in formulating such materials, up to about 15 wt % elemental carbon material can be dispersed in sulfur at temperatures high enough that the sulfur is molten, but low enough that significant ring opening and polysulfide polymerization does not occur (e.g., at temperatures in the range of about 120° C. to about 160° C.). Higher loadings of elemental carbon materials in sulfur can be achieved by pre-dissolution of the sulfur and dispersion of the elemental carbon material into a suitable solvent (e.g., carbon disulfide) followed by removal of the solvent under reduced pressure to yield a blended composite powder which can be melted and allowed to with the one or more monomers. To induce curing of the dispersed carbon, or other nanoinclusions with the sulfur matrix, direct heating of the dispersion above T=160° C., typically below 200° C. affords a polymerized nanocomposite.

As used herein, the term "thermoplastic polymer" refers to a polymer that can be softened and melted when heated and hardened when cooled. When softened or melted, this pliable polymer can be reshaped and molded. The thermoplastic polymer can undergo multiple melt-processing iterations to allow for re-working and recycling. Non-limiting examples of thermoplastic polymers include polyethylene, polypropylene, polyvinyl chloride (PVC), polystyrene, polyester, polycarbonate, polyamide (i.e. Nylon), polycarbonate, and poly(methyl methacrylate) (i.e. acrylics).

As used herein, the terms "those defined above" and "those defined herein" when referring to a variable incorporates by reference the broad definition of the variable as well as any narrow and/or preferred definitions, if any.

Figure 2:
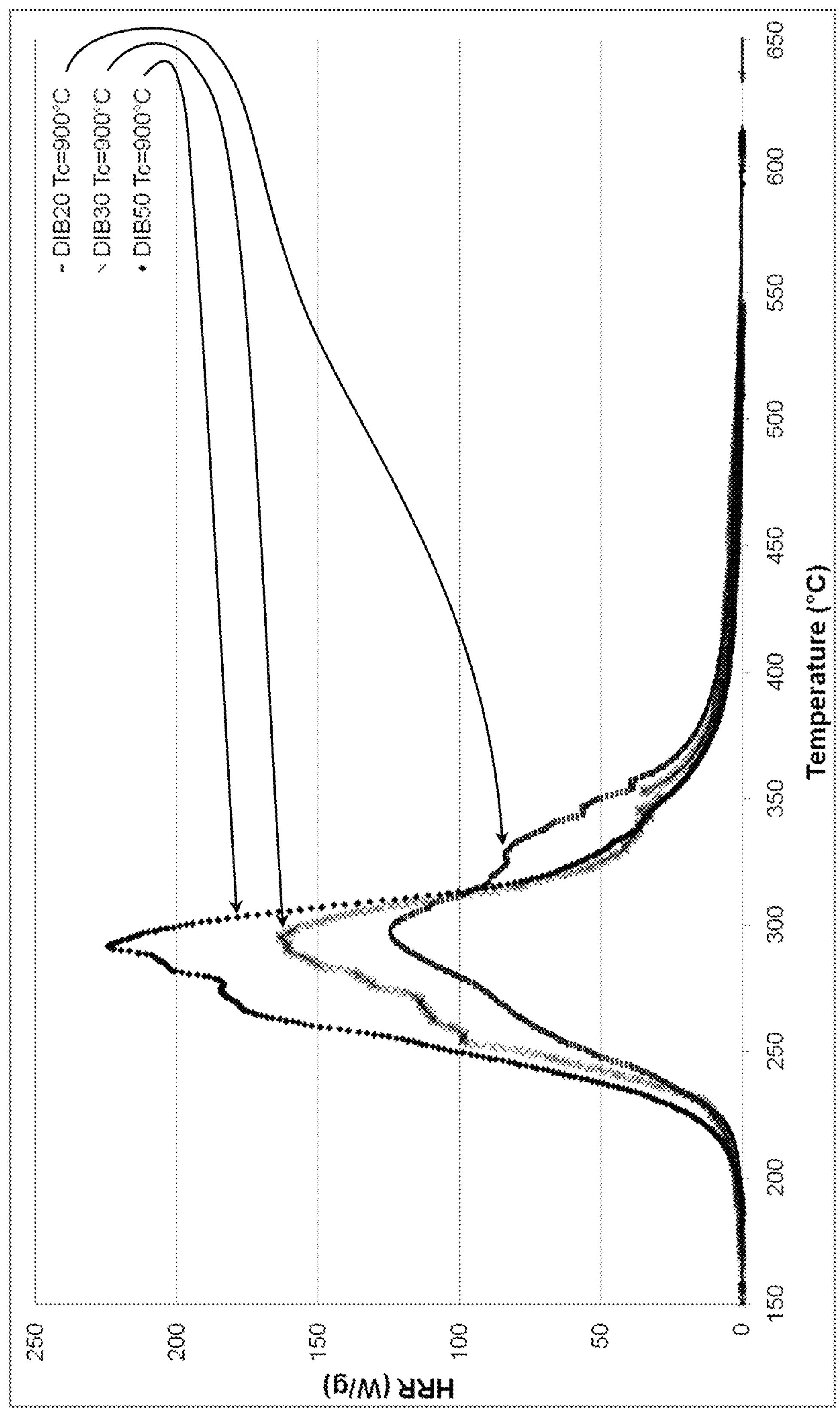
FIG. 2 shows an exemplary chart of temperature vs. heat release rate (HRR) for samples of the present invention at a combustor temperature of 900° C.
Figure 3:
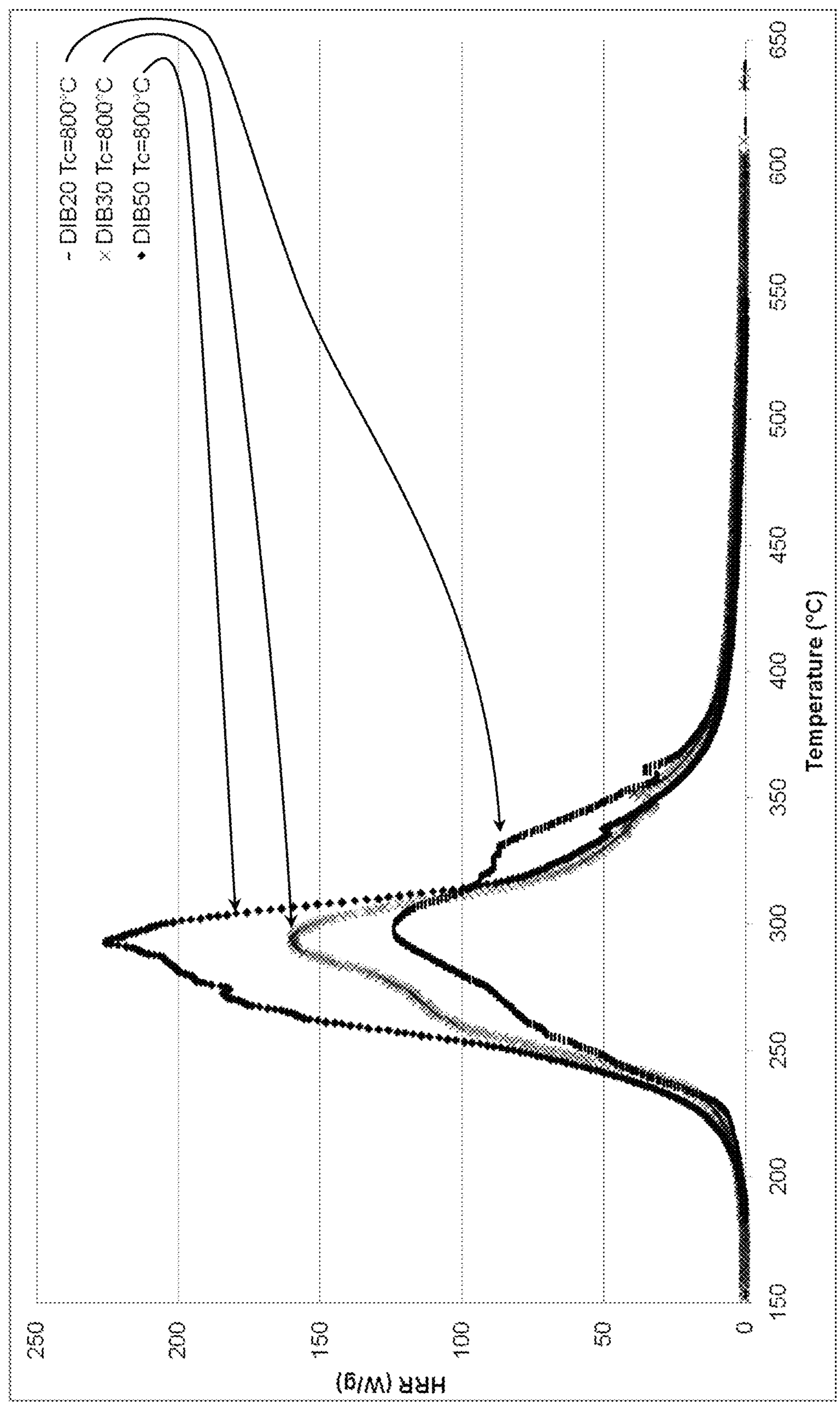
FIG. 3 shows an exemplary chart of temperature vs. heat release rate (HRR) for samples of the present invention at a combustor temperature of 800° C.

Referring now to FIGS. 1-3, in one embodiment, the present invention features a fire retardant composition comprising a polymeric blend of at least about 50 wt % of a thermoplastic polymer, and about 10-50 wt % of a sulfur copolymer. The sulfur copolymer may comprise at least about 40 wt % of sulfur monomers, and about 10-50 wt % of organic comonomers that are polymerized with the sulfur monomers. Without wishing to be bound by theory or mechanism, when a substrate combined with the fire retardant composition is on fire, the fire retardant composition can form a charring layer on a surface of the substrate that is effective for extinguishing the fire. In some embodiments, the charring layer comprises at least about 10 wt % char or at least about 20 wt % char. In other embodiments, the fire retardant composition may provide for test specimens that are combined with the fire retardant composition to exhibit a limiting oxygen index (LOI) of at least 25 and a UL94-V rating of V-1 or V-0.

In one embodiment, the polymeric blend may comprise about 50 wt % of the thermoplastic polymer and about 50 wt % of the sulfur copolymer. In one other embodiment, the polymeric blend may comprise about 60-90 wt % of the thermoplastic polymer and about 10-40 wt % of the sulfur copolymer. In another embodiment, the polymeric blend may comprise about 70-90 wt % of the thermoplastic polymer and about 10-30 wt % of the sulfur copolymer. In yet another embodiment, the polymeric blend may comprise about 80-90 wt % of the thermoplastic polymer and about 10-20 wt % of the sulfur copolymer.

In some embodiments, the polymeric blend of the thermoplastic polymer and sulfur copolymer may be prepared by solution blending, melt processing, or co-extrusion. In some embodiments, the thermoplastic polymer may comprise polyethylene, polypropylene, polyvinyl chloride, polystyrene, polyester, polycarbonate, polyamide, polycarbonate, or poly(methyl methacrylate). In other embodiments, the sulfur monomers are prepared from elemental sulfur ($S_8$). In a preferred embodiment, the organic comonomers are ethylenically unsaturated comonomers. The ethylenically unsaturated comonomers may be vinylic comonomers that include, but are not limited to, styrenic monomers or diisopropenylbenzene. In yet other embodiments, the flame resistant substrate may further comprise a flame retardant filler that can enhance char formation.

According to some embodiments, the present invention provides a flame resistant substrate comprising a base material combined with any of the fire retardant compositions described herein. In one embodiment, the fire retardant composition forms a fire retardant intumescent coating on a surface of the base material. In another embodiment, the fire retardant composition is mixed into the base material.

According to some embodiments, the present invention features a coating composition for a fire retardant intumescent coating. The composition may comprise a sulfur copolymer comprising sulfur monomers prepared from elemental sulfur, wherein the sulfur monomers are at least about 40 wt % of the sulfur copolymer; and organic comonomers at about 10 wt % to 50 wt % of the sulfur copolymer. The organic comonomers are polymerized with the sulfur monomers to form the sulfur copolymer. In preferred embodiments, the coating composition provides for test specimens that are coated with the intumescent coating to exhibit an LOI of at least 25 and a UL94-V rating of V-1 or V-0. When a substrate coated with said intumescent coating is on fire, the intumescent coating forms a charring layer on a surface of the substrate. The charring layer is effective for extinguishing and preventing the spread of the fire by preventing oxygen from fueling the fire.

According to another embodiment, the present invention features a fire retardant composition comprising a sulfur copolymer. The sulfur copolymer may comprise sulfur monomers prepared from elemental sulfur, wherein the sulfur monomers are at least about 40 wt % of the sulfur copolymer; and organic comonomers at about 10 wt % to 50 wt % of the sulfur copolymer wherein the organic comonomers are polymerized with the sulfur monomers. Preferably, the fire retardant composition provides for test specimens that are combined with the fire retardant composition to exhibit an LOI of at least 25 and a UL94-V rating of V-1 or V-0. When a substrate combined with the fire retardant composition is on fire, the fire retardant composition forms a charring layer on a surface of the substrate, effective for extinguishing and preventing spread of the fire. In one embodiment, the charring layer comprises at least about 20 wt % char.

In an exemplary embodiment, the sulfur copolymer may comprise at least about 40 wt % of sulfur monomers, and about 10-50 wt % of ethylenically unsaturated comonomers that are polymerized with the sulfur monomers. The ethylenically unsaturated comonomers may include vinylic comonomers such as styrenic monomers or diisopropenylbenzene.

In other embodiments, the organic comonomers may be selected from a group consisting of amine comonomers, thiol comonomers, sulfide comonomers, alkynylly unsaturated comonomers, epoxide comonomers, nitrone comonomers, aldehyde comonomers, ketone comonomers, and thiirane comonomers.

In some embodiments, the substrate is a fabric, a polymeric article, or a foam. For example, the substrate may be clothing, plastic-coated wire, an electronic device, or furniture such as mattresses. The substrate may be constructed from materials such as polyurethane, polystyrene, polyethylene, nylon, polyester, rayon, acetates, or combinations thereof.

In other embodiments, the compositions described herein may further comprise binders, fillers, or combinations thereof that are flame retardant and can enhance char formation. Suitable binders include organic binders, inorganic binders and mixtures of these two types of binders. For example, the organic binders may be provided as a solid, a liquid, a solution, a dispersion, a latex, or similar form. The organic binder may comprise a thermoplastic or thermoset binder, which after cure is a flexible material. Other embodiments of the filler material may include clay materials, such as bentonite or kaolinite, and fiber materials, such as ceramic fibers and polycrystalline fibers.

In yet another embodiment, the present invention features a method of enhancing char formation in a substrate. The method may comprise combining a base material with a fire retardant composition to form the substrate. Preferably, the substrate exhibits an LOI of at least 25 and a UL94-V rating of V-1 or V-0. In some embodiments, the fire retardant composition comprises a sulfur copolymer comprising sulfur monomers prepared from elemental sulfur, wherein the sulfur monomers are at least about 40 wt % of the sulfur copolymer; and organic comonomers at about 10 wt % to 50 wt % of the sulfur copolymer wherein the organic comonomers are polymerized with the sulfur monomers. In other embodiments, the fire retardant composition comprises a polymer blend of the thermoplastic polymer and the sulfur copolymer. Without wishing to limit the present invention, the fire retardant composition is effective in forming a charring layer on the substrate when the substrate is on fire. The charring layer can extinguish and prevent the fire from spreading. In some embodiments, the charring layer may comprise at least 20 wt % char. For example, the charring layer may comprise at least 25 wt % char or 30 wt % char.

In some embodiments, the step of combining the base material with the fire retardant composition comprises coating the base material with a coating comprising the fire retardant composition. In other embodiments, the step of combining the base material with the fire retardant composition comprises depositing the fire retardant composition on the surface of the base material. In still other embodiments, the step of combining the base material with the fire retardant composition may comprise mixing monomers of the base material with monomers of the fire retardant composition to form a comonomer mixture, polymerizing the comonomer mixture to form a flame resistant polymer, and molding the flame resistant polymer to a shape of the substrate.

Another embodiment of the present invention may feature a method of forming a flame retardant-treated polymeric article. The method may comprise providing a polymeric base substrate, providing a flame retardant material comprising any of the flame retardant compositions described herein, and depositing the flame retardant material on at least a portion of an outer surface of the polymeric base substrate to form the flame retardant-treated polymeric article. Preferably, the flame retardant-treated polymeric article provides for test specimens that exhibit an LOI of at least 25 and a UL94-V rating of V-1 or V-0. Preferably, when the flame retardant-treated polymeric article is on fire, the flame retardant material forms a charring layer on the flame retardant-treated polymeric article to extinguish the fire. The charring layer may comprise at least 20 wt % char.

Alternate embodiments of the present invention may feature a method of forming a flame resistant composite. The method may comprise providing a flame retardant material comprising any of the flame retardant compositions described herein, providing a base material, and mixing the flame retardant material with the base material to form the flame resistant composite. The flame retardant material can enhance char formation when flame resistant composite is on fire. In some embodiments, the composite may comprise between about 1.0 to 20.0 wt % of the flame retardant material. For example, the composite may comprise about 10 wt % of the flame retardant material. In some embodiments, the base material is a polymeric material.

EXAMPLE

The following is a non-limiting example of the present invention. It is to be understood that said example is not intended to limit the present invention in any way. Equivalents or substitutes are within the scope of the present invention.

Example 1. Preparation of Sulfur/Diisopropenylbenzene (DIB) Copolymer

To a glass vial equipped with a magnetic stir bar was added elemental sulfur (17.50 g, $6.82\times10^{-2}$ mol), which was heated at 185° C. in a thermostated oil bath until a molten phase was formed. DIB (7.5 g, 8.11 mL, $5.848\times10^{-2}$ mol) was then added to the molten sulfur medium via syringe. The resulting mixture was stirred at 185° C. until a deep cherry red liquid resulted. At this point, the liquid was poured from into a vial and cooled to room temperature to yield a poly(sulfur-random-(1,3-diisopropenylbenzene) (poly(S-r-DIB)) copolymer with 30 wt % DIB.

Referring now to FIG. 1, sulfur copolymers of sulfur monomers and organic comonomers, namely diisopropenylbezene (DIB), were prepared in varying ratios in accordance with the procedure described above. For example, DIB20 refers to 80 wt % sulfur and 20 wt % DIB. Samples of the sulfur copolymers were burned at a combustor temperature of Tc=800° C. Residues thereof are the blackened areas shown in FIG. 1. This experiment demonstrates that sulfur copolymers having higher sulfur content are more effective fire retardants. The residue of DIB20 shows a significantly smaller charring layer than DIB30 or DIB50, which indicates that the charring layer of DIB20 extinguished and prevented the fire from spreading further.

The peak heat release rate (HRR) is a numerical indicator of the intensity of a fire; hence, it is desirable that the peak heat release rate of a flame retarded system be lower than that of the non-flame retarded system. Effective flame retardants are capable of lowering the heat released in a fire. FIG. 2 and TABLE 1 below shows exemplary char and energy data for pyrolysis of the sulfur copolymer samples at a combustor temperature of Tc=900° C. FIG. 3 and TABLE 2 below shows exemplary char and energy data for pyrolysis of the sulfur copolymer samples at a combustor temperature of Tc=800° C. DIB20 had a significantly smaller heat release rate (HRR) and heat release capacity (HRC) than DIB30 or DIB50, which again indicates that sulfur copolymers with higher sulfur content are effective flame retardants.

TABLE 1 shows exemplary char and energy data for pyrolysis of the copolymer material.

T combustor 900° C._T pyrolyzer from 70° C. to 900° C._O2 = 20% N2 = 80%

| Sample ID | Weight (mg) | Residue (%) | THR (kJ/g) | HRC (J/gK) | Peak max (° C.) |
|---|---|---|---|---|---|
| DIB20 | 4.549 | 13.0% | 11.6 | 126 | 295 |
| DIB30 | 4.375 | 18.4% | 12.3 | 163 | 293 |
| DIB50 | 4.649 | 25.4% | 15.5 | 231 | 291 |

TABLE 2 shows exemplary char and energy data for pyrolysis of the copolymer material.

T combustor 800° C._T pyrolyzer from 70° C. to 900° C._O2 = 20% N2 = 80%

| Sample ID | Weight (mg) | Residue (%) | THR (kJ/g) | HRC (J/gK) | Peak max (° C.) |
|---|---|---|---|---|---|
| DIB20 | 4.733 | 13.4% | 11.4 | 124 | 295 |
| DIB30 | 4.868 | 19.2% | 12.2 | 160 | 293 |
| DIB50 | 4.835 | 25.5% | 15.4 | 226 | 293 |

Example 2. Preparation of Thermoplastic/Sulfur Copolymer Blend

In one embodiment, the DIB30 sulfur copolymer of Example 1 is blended with polyethylene by co-extrusion such that a polymer blend with 10 wt % of DIB30 sulfur copolymer is produced. The polymer blend is then formed into a desired shape using a mold or injection molding and the resulting structure is flame-resistant.

Example 3. Preparation of Thermoplastic/Sulfur Copolymer Blend

In another embodiment, the DIB30 sulfur copolymer of Example 1 is blended with polyester by melt processing such that a polymer blend with 20 wt % of DIB30 sulfur copolymer is produced. The polymer blend is then extruded and spun into a thread that can be used in making flame-resistant fabrics.

Example 4. Preparation of Thermoplastic/Sulfur Copolymer Blend

In yet another embodiment, the DIB30 sulfur copolymer of Example 1 is blended with polystyrene by solution processing such that a polymer blend with 15 wt % of DIB30 sulfur copolymer is produced. A wooden board is spray-coated with the polymer blend to make the board flame-resistant.

Example 5. Preparation of Flame-Resistant Material

In some embodiments, the DIB30 sulfur copolymer of Example 1 is used to form a flame-retardant coating. A pipe is dipped in the copolymer to coat the surface of the pipe, thereby making the pipe flame-resistant.

Example 6. Preparation of Flame-Resistant Material

In other embodiments, the DIB30 sulfur copolymer of Example 1 is applied to a door or window such that the copolymer acts as a gasket. In the event of a fire, the gasket acts as a fire and smoke seal.

Additional aspects of the sulfur polymers are described below. In some embodiments, the sulfur copolymer is produced by providing elemental sulfur, heating the elemental sulfur into molten sulfur, and adding organic comonomers to the molten sulfur, thereby forming the sulfur copolymer.

For example, a mixture including sulfur and the organic monomers is heated together at a temperature sufficient to initiate polymerization (i.e., through free radical polymerization, through anionic polymerization, or through both, depending on the monomers used). In some embodiments, the mixture including sulfur and the organic monomers is heated together at a temperature in the range of about 120° C. to about 230° C., e.g., in the range of about 120° C. to 140° C. or about 160° C. to 230° C. The person of skill in the art will select conditions that provide the desired level of polymerization. In one embodiment, the mixture comprising sulfur and organic monomers is formed by first heating a mixture comprising sulfur to form a molten sulfur, then adding the organic monomers to the molten sulfur. In certain embodiments, the polymerization reaction is performed under ambient pressure. However, in other embodiments, the polymerization reaction can be performed at elevated pressure (e.g., in a bomb or an autoclave). Elevated pressures can be used to polymerize more volatile monomers so that they do not vaporize under elevated temperature reaction conditions.

The sulfur can be provided as elemental sulfur, for example, in powdered form. Under ambient conditions, elemental sulfur primarily exists in an eight-membered ring form ($S_8$) which melts at temperatures in the range of 120-124° C. and undergoes an equilibrium ring-opening polymerization (ROP) of the $S_8$ monomer into a linear polysulfane with diradical chain ends.

As the person of skill in the art will appreciate, while $S_8$ is generally the most stable, most accessible and cheapest feedstock, many other allotropes of sulfur can be used (such as other cyclic allotropes, derivable by melt-thermal processing of $S_8$). Any sulfur species that yield diradical or anionic polymerizing species when heated as described herein can be used in practicing the present invention.

Because both anionic and radical polymerization can occur in the polymerization reaction mixtures, any desirable combination of amine monomers, thiol monomers, sulfide monomers, alkynylly unsaturated monomers, nitrone and/or nitroso monomers, aldehyde monomers, ketone monomers, thiirane monomers, ethylenically unsaturated monomers, and/or epoxide monomers can be used in the copolymers.

In other embodiments, the sulfur copolymer may further comprise one or more polyfunctional comonomers selected from a group consisting of polyvinyl comonomers, polyisopropenyl comonomers, polyacryl comonomers, polymethacryl comonomers, polyunsaturated hydrocarbon comonomers, polyepoxide comonomers, polythiirane comonomers, polyalkynyl comonomers, polydiene comonomers, polybutadiene comonomers, polyisoprene comonomers, polynorbornene comonomers, polyamine comonomers, polythiol comonomers, polysulfide comonomers, polyalkynylly unsaturated comonomers, polynitrone comonomers, polyaldehyde comonomers, polyketone comonomers, and polyethylenically unsaturated comonomers. The polyfunctional comonomers may be present in an amount ranging from about 0.5 wt % to 1 wt %, or about 1 wt % to 5 wt %, or about 5 wt % to 15 wt %, or about 15 wt % to 25 wt %, or about 25 wt % to 35 wt %, or about 35 wt % to 45 wt %, or about 45 wt % to 50 wt %.

In some embodiments, the sulfur copolymer as described herein may comprise sulfur monomers at a level of at least about 5 wt % of the sulfur copolymer. The sulfur copolymer may comprise sulfur monomers at a level of at least about 10 wt %, or at least about 20 wt %, or at least about 30 wt %, or at least about 40 wt %, or at least about 50 wt %, or at least about 60 wt %, or at least about 70 wt %, or at least about 80 wt %, or at least about 90 wt % of the sulfur copolymer. For example, the sulfur monomers may be about 50 wt %, or about 60 wt %, or about 70 wt %, or about 80 wt %, or about 90 wt %, or about 95 wt % of the sulfur copolymer. In other embodiments, the sulfur copolymer as described herein may comprise sulfur monomers at a level in the range of about 5 to about 10 wt % of the sulfur copolymer. The sulfur copolymer may comprise sulfur monomers at a level in the range of about 10 to 20 wt %, or in the range of about 20 to 30 wt %, or in the range of about 30 to 40 wt %, or in the range of about 40 to 50 wt %, or in the range of about 50 to 60 wt %, or in the range of about 60 to 70 wt %, or in the range of about 70 to 80 wt %, or in the range of about 80 to 90 wt %, or in the range of about 90 to 95 wt % of the sulfur copolymer.

In some embodiments, the sulfur copolymer as described herein may comprise organic comonomers at a level of at least 0.1 wt % of the sulfur copolymer. The sulfur copolymer may comprise organic comonomers at a level of at least about 0.5 wt %, or at least about 1 wt %, or at least about 5 wt %, or at least about 10 wt %, or at least about 20 wt %, or at least about 30 wt %, or at least about 40 wt %, or at least about 50 wt %, or at least about 60 wt % of the sulfur copolymer. For example, the organic comonomers may be about 5 wt %, or about 10 wt %, or about 20 wt %, or about 30 wt %, or about 40 wt %, or about 50 wt % of the sulfur copolymer. In other embodiments, the sulfur copolymer as described herein may comprise organic comonomers at a level in the range of about 0.1 wt % to 0.5 wt % of the sulfur copolymer. The sulfur copolymer may comprise organic comonomers at a level in the range of about 0.5 wt % to 1 wt %, or about 1 wt % to 5 wt %, or about 5 wt % to 15 wt %, or about 15 wt % to 25 wt %, or about 25 wt % to 35 wt %, or about 35 wt % to 45 wt %, or about 45 wt % to 55 wt %, or about 55 wt % to 65 wt % of the sulfur copolymer.

In some embodiments, the sulfur copolymer may further comprise up to about 50 wt % elemental carbon material dispersed in the sulfur copolymer. For example, the sulfur copolymer may comprise the elemental carbon material at a level in the range of about 10 to 20 wt %, or in the range of about 20 to 30 wt %, or in the range of about 30 to 40 wt %, or in the range of about 40 to 50 wt % of the sulfur copolymer.

In certain embodiments, it can be desirable to use a nucleophilic viscosity modifier in liquefying the elemental sulfur when preparing the sulfur monomers, for example, before adding the comonomers. The nucleophilic viscosity modifier can be, for example, a phosphorus nucleophile (e.g., a phosphine), a sulfur nucleophile (e.g., a thiol) or an amine nucleophile (e.g., a primary or secondary amine). When elemental sulfur is heated in the absence of a nucleophilic viscosity modifier, the elemental sulfur rings can open to form sulfur radicals that can combine to form linear polysulfide chains, which can provide a relatively high overall viscosity to the molten material. Nucleophilic viscosity modifiers can break these linear chains into shorter lengths, thereby making shorter polysulfides that lower the overall viscosity of the molten material, making the sulfur monomers easier to mix with other species, and easier to stir for efficient processing. Some of the nucleophilic viscosity modifier will react to be retained as a covalently bound part of the copolymer, and some will react to form separate molecular species, with the relative amounts depending on nucleophile identity and reaction conditions. While some of the nucleophilic viscosity modifier may end up as a separate molecular species from the polymer chain, as used herein, nucleophilic viscosity modifiers may become part of the copolymer. Non-limiting examples of nucleophilic viscosity modifiers include triphenylphosphine, aniline, benzenethiol, and N,N-dimethylaminopyridine. Nucleophilic viscosity modifiers can be used, for example, in an amount up to about 5 wt %, or even up to about 10 wt % of the sulfur copolymer. When a nucleophilic viscosity modifier is used, in certain embodiments it can be used in the range of about 1 wt % to about 10 wt % of the sulfur copolymer As used herein, the term "about" refers to plus or minus 10% of the referenced number. For example, about 50 wt % refers to 45 wt %-55 wt %. Various modifications of the invention, in addition to those described herein, will be apparent to those skilled in the art from the foregoing description. Such modifications are also intended to fall within the scope of the appended claims. Each reference cited herein is incorporated by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A fire retardant composition comprising a polymeric blend of:

a. at least about 50 wt % of a thermoplastic polymer; and b. about 10-50 wt % of a sulfur copolymer, the sulfur copolymer comprising at least about 40 wt % of sulfur monomers, and about 10-50 wt % of ethylenically unsaturated comonomers, wherein the comonomers are polymerized with the sulfur monomers;

wherein when a substrate combined with the fire retardant composition is on fire, the fire retardant composition forms a charring layer on a surface of the substrate that is effective for extinguishing the fire.

2. The fire retardant composition of claim 1, wherein the charring layer comprises at least about 10 wt % char.

3. The fire retardant composition of claim 1, wherein the fire retardant composition provides for test specimens that are combined with the fire retardant composition to exhibit a limiting oxygen index (LOI) of at least 25 and a UL94-V rating of V-1 or V-0.

4. The fire retardant composition of claim 1, wherein the sulfur monomers are prepared from elemental sulfur.

5. The fire retardant composition of claim 1, wherein the ethylenically unsaturated comonomers are vinylic comonomers.

6. The fire retardant composition of claim 5, wherein the vinylic comonomers are styrenic monomers or diisopropenylbenzene.

7. The fire retardant composition of claim 1, wherein the polymeric blend of the thermoplastic polymer and sulfur copolymer is prepared by solution blending, melt processing, or co-extrusion.

8. The fire retardant composition of claim 1, wherein the thermoplastic polymer comprises polyethylene, polypropylene, polyvinyl chloride, polystyrene, polyester, polycarbonate, polyamide, polycarbonate, or poly(methyl methacrylate).

9. The flame resistant substrate of claim 1 further comprising a flame retardant filler to enhance char formation.

10. A flame resistant substrate comprising a base material combined with the fire retardant composition of claim 1.

11. The flame resistant substrate of claim 10, wherein the fire retardant composition forms a fire retardant intumescent coating on a surface of the base material.

12. The flame resistant substrate of claim 10, wherein the fire retardant composition is mixed into the base material.

* * * * *